US011452559B2

(12) United States Patent
Prior et al.

(10) Patent No.: US 11,452,559 B2
(45) Date of Patent: *Sep. 27, 2022

(54) ELECTROSURGICAL PLUG FOR ENERGY ACTIVATION OF SURGICAL INSTRUMENTS

(71) Applicant: COVIDIEN LP, Mansfield, MA (US)

(72) Inventors: Scott J. Prior, Shelton, CT (US); Jacob C. Baril, Norwalk, CT (US); Christopher M. Meehan, New Haven, CT (US); Saumya Banerjee, Hamden, CT (US); Amy L. Kung, Hamden, CT (US); Thomas A. Zammataro, Hamden, CT (US); Ernest A. Addi, Middletown, CT (US)

(73) Assignee: Covidien LP, Mansfield, MA (US)

( * ) Notice: Subject to any disclaimer, the term of this patent is extended or adjusted under 35 U.S.C. 154(b) by 559 days.

This patent is subject to a terminal disclaimer.

(21) Appl. No.: 16/451,338

(22) Filed: Jun. 25, 2019

(65) Prior Publication Data
US 2020/0405371 A1     Dec. 31, 2020

(51) Int. Cl.
*A61B 18/14*     (2006.01)
*A61B 18/12*     (2006.01)
(Continued)

(52) U.S. Cl.
CPC ...... *A61B 18/1233* (2013.01); *A61B 18/1402* (2013.01); *A61B 18/1442* (2013.01);
(Continued)

(58) Field of Classification Search
CPC ...... A61B 2018/00178; H01R 2201/12; H01R 9/24; H01R 9/2425; H01R 9/2433;
(Continued)

(56) References Cited

U.S. PATENT DOCUMENTS 1,996,258 A     4/1935   Ruskin
2,051,169 A     8/1936   Handschug
(Continued)

FOREIGN PATENT DOCUMENTS

DE     2646229 A1     4/1978
EP     2329783 A1     6/2011
(Continued)

OTHER PUBLICATIONS

Extended European Search Report issued in corresponding European Application No. 20182166.7 dated Nov. 27, 2020, 7 pages.
(Continued)

*Primary Examiner* — Joanne M Hoffman
*Assistant Examiner* — Sean W Collins
(74) *Attorney, Agent, or Firm* — Carter, DeLuca & Farrell LLP

(57) ABSTRACT

An electrosurgical system includes an electrosurgical generator having active and return terminals, an electrosurgical instrument including an active electrode, a return instrument including a return electrode, an active plug configured to connect to the active terminal of the generator, a return plug configured to connect to the return terminal of the generator, an active cable extending from the return plug to the electro surgical instrument, a return cable extending from the return plug to the return instrument, a connector cable extending from the active plug to the return plug, and a mechanical switch mechanism disposed within the return plug. The mechanical switch mechanism has a disengaged position in which the active plug is electrically disconnected from the active cable and an engaged position in which the active plug is in electrical communication with the active cable.

19 Claims, 7 Drawing Sheets

(51) Int. Cl.
    *A61B 17/00* (2006.01)
    *A61B 18/00* (2006.01)
    *H01R 24/00* (2011.01)
    *H01R 13/703* (2006.01)
    *H01R 13/502* (2006.01)

(52) U.S. Cl.
    CPC ..... *A61B 18/12* (2013.01); *A61B 2017/00477* (2013.01); *A61B 2018/00178* (2013.01); *A61B 2018/00196* (2013.01); *A61B 2018/00589* (2013.01); *A61B 2018/00595* (2013.01); *A61B 2018/00601* (2013.01); *A61B 2018/1253* (2013.01); *A61B 2018/146* (2013.01); *H01R 13/502* (2013.01); *H01R 13/703* (2013.01); *H01R 24/00* (2013.01); *H01R 2201/12* (2013.01)

(58) Field of Classification Search
    CPC .. H01R 13/70; H01R 13/703; H01R 13/7036; H01R 33/96
    See application file for complete search history.

(56) References Cited

U.S. PATENT DOCUMENTS

| | | | |
|---|---|---|---|
| 4,758,184 A | 7/1988 | Call | |
| 5,160,334 A | 11/1992 | Billings et al. | |
| 5,312,401 A | 5/1994 | Newton et al. | |
| 5,400,267 A | 3/1995 | Denen et al. | |
| 5,611,798 A | 3/1997 | Eggers | |
| 5,688,269 A | 11/1997 | Newton et al. | |
| 5,830,212 A | 11/1998 | Cartmell et al. | |
| 6,063,075 A | 5/2000 | Mihori | |
| 6,190,385 B1 | 2/2001 | Tom et al. | |
| 6,203,541 B1 | 3/2001 | Keppel | |
| 6,237,604 B1 | 5/2001 | Burnside et al. | |
| 6,350,139 B1 | 2/2002 | Haag | |
| 6,409,722 B1 | 6/2002 | Hoey et al. | |
| 6,522,234 B1 | 2/2003 | Sturgill | |
| 6,537,272 B2 | 3/2003 | Christopherson et al. | |
| 6,644,986 B1 | 11/2003 | Wilker, Sr. | |
| 6,736,810 B2 | 5/2004 | Hoey et al. | |
| 6,849,073 B2 | 2/2005 | Hoey et al. | |
| 6,958,463 B1 | 10/2005 | Kochman et al. | |
| 7,041,096 B2 | 5/2006 | Malis et al. | |
| 7,169,144 B2 | 1/2007 | Hoey et al. | |
| 9,566,109 B2 | 2/2017 | Hart et al. | |
| 2005/0239349 A9 | 10/2005 | Desinger | |
| 2005/0283148 A1 | 12/2005 | Janssen et al. | |
| 2007/0049914 A1 | 3/2007 | Eggleston | |
| 2009/0061667 A1 | 3/2009 | Grieff | |
| 2009/0065565 A1 | 3/2009 | Cao | |
| 2010/0136856 A1 | 6/2010 | Gleason et al. | |
| 2010/0280511 A1 | 11/2010 | Rachlin et al. | |
| 2011/0312207 A1 | 12/2011 | Chapel et al. | |
| 2013/0274734 A1 | 10/2013 | Maass et al. | |
| 2013/0289559 A1 | 10/2013 | Reid, Jr. | |
| 2014/0088593 A1* | 3/2014 | Van Wyk | A61B 18/12 606/41 |
| 2015/0126998 A1* | 5/2015 | Batchelor | A61B 18/1445 606/42 |
| 2015/0171569 A1 | 6/2015 | Maass et al. | |
| 2015/0342667 A1* | 12/2015 | Cornacchia | A61B 18/1442 606/51 |
| 2016/0045247 A1 | 2/2016 | Heim et al. | |

FOREIGN PATENT DOCUMENTS

| | | |
|---|---|---|
| EP | 2689738 A1 | 1/2014 |
| WO | 9300862 A2 | 1/1993 |
| WO | 2005060365 A2 | 7/2005 |
| WO | 2005081730 A2 | 9/2005 |
| WO | 2007136694 A2 | 11/2007 |
| WO | 2013158537 A2 | 10/2013 |
| WO | 2018217429 A1 | 11/2018 |

OTHER PUBLICATIONS

Extended European Search Report issued in corresponding European Application No. EP 20182199.8 dated Nov. 12, 2020, 10 pages.

* cited by examiner

ELECTROSURGICAL PLUG FOR ENERGY ACTIVATION OF SURGICAL INSTRUMENTS

BACKGROUND

1. Technical Field

The present disclosure relates to electrosurgical instruments and, more specifically, to a plug for electrosurgical instruments.

2. Discussion of Related Art

Electrosurgical devices have become widely used by surgeons. Electrosurgical devices may include monopolar hand-held instruments, e.g., pencils, which transfer radio-frequency (RF) electrical energy to a tissue site from a suitable electrosurgical generator. The electrical energy may be returned to the source via a return electrode pad positioned under a patient, or another return electrode positioned in bodily contact, with or immediately adjacent to, the surgical site. The waveforms which result from the RF electrical current may be used to produce a variety of effects such as, for example, surgical cutting, coagulation, cauterization, etc.

Electrosurgical generators include an active connector for the active electrode of the electrosurgical device and a return connector for the return electrode, e.g., the return pad or other return electrode. To ensure that electrosurgical energy takes the desired path and has the desired effect during a surgical procedure, it is important to ensure that both the electrosurgical device and the return electrode are properly connected to the electrosurgical generator before supplying energy to the active electrode.

SUMMARY

The present disclosure relates generally to a plug configured to prevent activation of the active electrode until the return electrode is properly connected to the electrosurgical generator. As used herein, the term "clinician" refers to a doctor, a nurse, or any other care provider and may include support personnel. Throughout this description, the term "proximal" refers to the portion of the device or component thereof that is closer to the clinician and the term "distal" refers to the portion of the device or component thereof that is farther from the clinician. Further, to the extent consistent, any of the aspects detailed herein may be used in conjunction with any of the other aspects detailed herein.

An electrosurgical system provided in accordance with the present disclosure includes an electrosurgical generator including an active terminal and a return terminal, an electrosurgical instrument including an active electrode, a return instrument including a return electrode, an active plug configured to connect to the active terminal of the electrosurgical generator, a return plug configured to connect to the return terminal of the electrosurgical generator to electrically couple the return electrode to the return terminal, an active cable extending from the return plug to the electrosurgical instrument and disposed in electrical communication with the active electrode, a return cable extending from the return plug to the return instrument, a connector cable extending from the active plug to the return plug, and mechanical switch mechanism disposed within the return plug. The mechanical switch mechanism has a disengaged position in which the active plug is electrically disconnected from the active cable and an engaged position in which the active plug is in electrical communication with the active cable.

In an aspect of the present disclosure, the mechanical switch mechanism is in the disengaged position when the return plug is disconnected from the return terminal and is in the engaged position when the return plug is connected to the return terminal.

In another aspect of the present disclosure, the mechanical switch mechanism includes a plunger translatable within the return plug. The plunger includes a tip portion extending from a leading end of the return plug in the disengaged position and disposed within the return plug in the engaged position.

In yet another aspect of the present disclosure, the tip portion is configured to engage the return terminal as the return plug is connected to the return terminal such that engagement between the tip portion and the return terminal transitions the mechanical switch mechanism from the disengaged position to the engaged position.

In still another aspect of the present disclosure, the return plug includes a post and the plunger includes a slot defined therethrough. The post is received within the slot to limit translation of the plunger towards and away from the leading end of the return plug.

In still yet another aspect of the present disclosure, the return plug defines a plunger channel within which the plunger is slidably received.

In another aspect of the present disclosure, the mechanical switch mechanism includes a bar conductor extending across the plunger channel that is electrically coupled to the active cable.

In still another aspect of the present disclosure, the plunger includes a protrusion having a contact on a surface facing a trailing end of the return plug. The contact is spaced apart from the bar conductor in the disengaged position and in contact with the bar conductor in the engaged position.

In yet another aspect of the present disclosure, in the engaged position, engagement between the contact and the bar conductor bends the bar conductor towards the trailing end of the return plug.

In another aspect of the present disclosure, the active plug includes an active lead that extends into the return plug and is coupled to the plunger in electrical communication with the contact. The active lead may be connected to a leading surface of the protrusion opposite the contact.

In still yet another aspect of the present disclosure, the mechanical switch mechanism includes a biasing member disposed within the plunger channel and engaged with the plunger to urge the plunger towards the leading end of the return plug.

In an aspect of the present disclosure, the bar conductor is a leaf spring.

A return plug for an electrosurgical system provided in accordance with the present disclosure includes a mechanical switch mechanism for mechanically connecting an active lead configured to electrically connect to an active terminal of an electrosurgical generator to an active cable configured to electrically connect to an active electrode of an electrosurgical instrument when the return plug is connected to a return terminal of the electrosurgical generator and to electrically disconnect the active lead from the active cable when the return plug is not connected to the return terminal.

In an aspect of the present disclosure, the return plug includes an upper housing and a lower housing defining a pair of return channels and a plunger channel defined between the pair of return channels. Each of the return channels extends through a leading end and a trailing end of the upper and lower housings.

In another aspect of the present disclosure, the mechanical switch mechanism includes a plunger slidably disposed within the plunger channel. The plunger includes a slot defined therethrough configured to allow translation of the plunger between a first position in which the active lead is electrically disconnected from the active cable and a second position in which the active lead is electrically connected to the active cable. The plunger may be biased towards the first position.

Another surgical system provided in accordance with the present disclosure includes an active terminal, a return terminal, an active electrode, a return electrode, an active plug configured to connect to the active terminal, and a return plug configured to connect to the return terminal. The return plug is coupled to the return electrode and coupled between the active plug and the active electrode. The return plug is configured to break an electrical connection between the active plug and the active electrode when the return plug is not connected to the return terminal and to establish an electrical connection between the active plug and the active electrode when the return plug is connected to the return terminal.

In an aspect of the present disclosure, the system includes an electrosurgical generator including the active and return terminals.

In another aspect of the present disclosure, upon connection of the return plug with the return terminal, a mechanical switch of the return plug is actuated to establish the electrical connection between the active plug and the active electrode.

In another aspect of the present disclosure, the mechanical switch of the return plug includes a plunger configured to bring at first contact into electrical communication with a second contact upon connection of the return plug with the return terminal to establish the electrical connection between the active plug and the active electrode.

In still another aspect of the present disclosure, the mechanical switch of the return plug includes a plunger configured to displace an interrupting structure to bring first and second contacts into electrical communication with one another upon connection of the return plug with the return terminal to establish the electrical connection between the active plug and the active electrode.

In yet another aspect of the present disclosure, the first and second contacts are biased towards a contacting position such that, upon displacement of the interrupting structure, the first and second contacts are biased into contact with one another.

In still yet another aspect of the present disclosure, the first and second contacts are spring contacts.

In another aspect of the present disclosure, the system further includes an active cable extending from the return plug to the active electrode, a return cable extending from the return plug to the return electrode, and a connector cable extending from the active plug to the return plug.

In yet another aspect of the present disclosure, the active electrode forms part of a monopolar pencil. Additionally or alternatively, the return electrode forms part of a return tenaculum.

A surgical device provided in accordance with the present disclosure includes a first arm having a proximal handle portion, a distal grasping portion, and a pivot portion positioned between the handle portion and the grasping portion. The surgical device further includes a second arm having a proximal handle portion, a distal grasping portion, and a pivot portion positioned between the handle portion and the grasping portion. The first and second arms are pivotally coupled to one another at the pivot portions such that as the handle portions move towards one another the grasping portions move towards one another. An opening mechanism is disposed between the handle portions, and includes a first portion secured to the handle portion of the first arm, a second portion slidably secured to the handle portion of the second arm, and a central portion interconnecting the first and second portions. The central portion is positioned adjacent the pivot portions and configured to urge the first and second portions apart from one another.

In an aspect of the present disclosure, the second portion includes a slot defined in a longitudinal direction of the second arm. The slot is configured to receive a fastener configured to secure the second portion to the second arm. The fastener has a locked configuration in which the second portion is fixed to the second arm and the handle portions of the first and second arms are fixed relative to one another.

In another aspect of the present disclosure, the first arm includes a return cable that is in electrical communication with the grasping portions of the first and second arms. The grasping portions are configured to function as return electrodes for a monopolar electrosurgical device.

BRIEF DESCRIPTION OF THE DRAWINGS

Various aspects and features of the present disclosure are described hereinbelow with reference to the drawings, which are incorporated in and constitute a part of this specification, wherein like reference numerals designate identical or corresponding elements in each of the several views.

DETAILED DESCRIPTION

Figure 1:
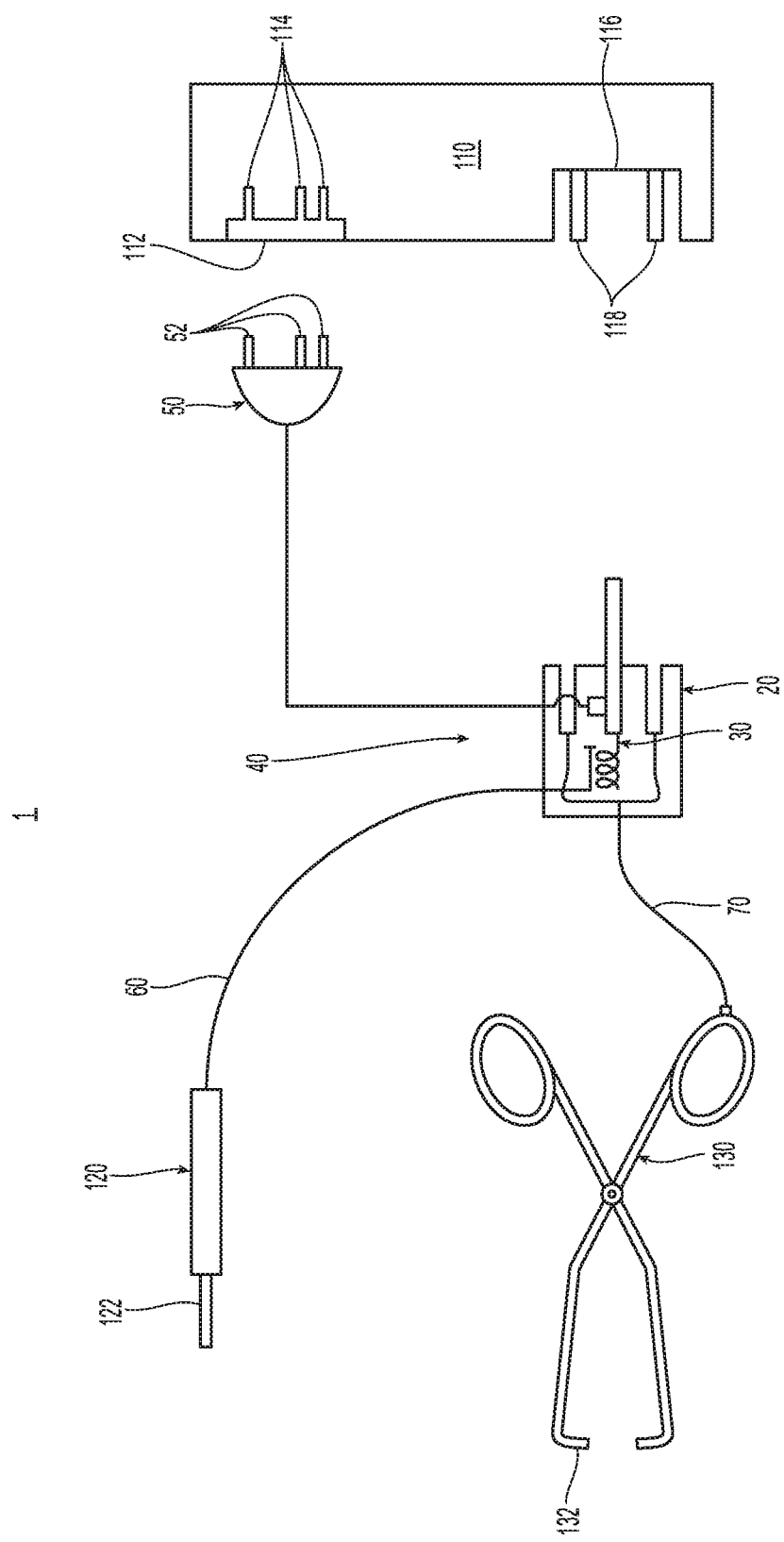
FIG. 1 is a schematic illustration of an exemplary electrosurgical system provided in accordance with the present disclosure.

Referring to FIG. 1, an electrosurgical system 1 is provided in accordance with the present disclosure and includes an electrosurgical generator 110, an electrosurgical device 120, a return device 130, and a cable system 40. The electrosurgical generator 110 is configured to provide electrosurgical energy for treating tissue and includes an active terminal 112 and a return terminal 116. The active terminal 112 includes one or more receptacles 114 and the return terminal 116 includes one or more prongs 118 for electrically coupling to the electrosurgical generator, although other configurations are also contemplated, e.g., wherein the active terminal 112 additionally or alternatively includes prongs and/or the return terminal 116 additionally or alternatively includes receptacles.

The electrosurgical device 120 may be configured as a monopolar device, e.g., a pencil, and includes an active electrode 122 that is configured to deliver electrosurgical energy to tissue. The return device 130 includes a return electrode 132 configured to provide a return path for electrosurgical energy delivered by the active electrode 122 to return to the electrosurgical generator 110, thus defining a monopolar surgical system although bipolar configurations are also contemplated. As shown, the return device 130 is configured as a tenaculum that is insertable into a surgical site adjacent the electrosurgical device 120 and the active electrode 122 thereof. In some embodiments, the return device 130 may be a return pad that is in contact with a portion of the skin of the patient or may be a return electrode in contact with the skin of the patient adjacent a surgical site.

The cable system 40 is configured to electrically couple the active and return electrodes 122, 132 to the electrosurgical generator 110. The cable system 40 includes a return plug 20, an active plug 50, an active cable 60, and a return cable 70. The active plug 50 is complementary to the active terminal 112 of the electrosurgical generator 110, e.g., the active plug 50 includes one or more prongs 52 that are configured to be received within the receptacles 114 of the active terminal 112 of the electrosurgical generator 110. The active plug 50 is connected to the return plug 20 via a connector cable 58 and indirectly coupled to the electrosurgical device 120 thereby, as detailed below. Thus, the active plug 50 is not directly connected to the electrosurgical device 120.

The active cable 60 extends between and interconnects the return plug 20 and the electrosurgical device 120. The active cable 60 may be integrally connected with the return plug 20 and/or the electrosurgical device 120 or the active cable 60 may be releaseably connected to the return plug 20 and/or the electrosurgical device 120. For example, the active cable 60 may have a plug (not shown) and the return plug 20 may include a receptacle (not shown) for receiving the plug, or vice versa, to electrically couple the active cable 60 to the return plug 20.

The return cable 70 extends from the return plug 20 to the return device 130. The return cable 70 is integrally connected with the return plug 20 and the return device 130 such that the return cable 70 is non-removable from both the return plug 20 and the return device 130. Integrally connecting the return cable 70 with the return plug 20 and the return device 130 requires the return electrode 132 to be in electrical communication with the electrosurgical generator 110 during delivery of electrosurgical energy to the active electrode 122, as detailed below.

Figure 2:
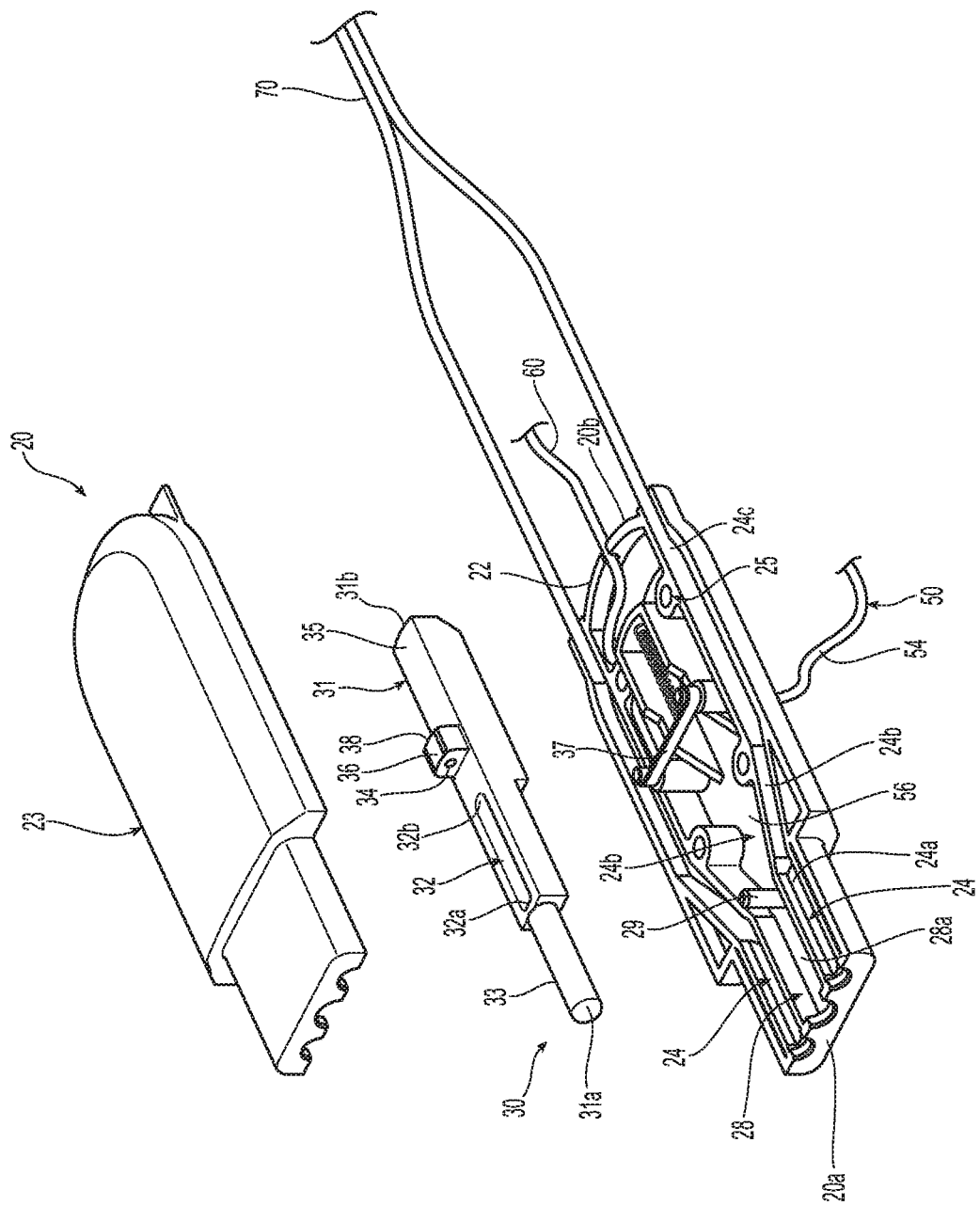
FIG. 2 is a perspective view, with parts separated, of a plug of the electrosurgical system of FIG. 1.

With additional reference to FIG. 2, the return plug 20 includes a mechanical switch mechanism 30 to electrically couple the active plug 50 with the active cable 60 when the return plug 20 is connected to the return terminal 116 of the electrosurgical generator 110 such that electrosurgical energy can be delivered to tissue by the active electrode 122. The mechanical switch mechanism 30 prevents delivery of electrosurgical energy to the active electrode 122 when the return plug 20 is not connected to the return terminal 116.

The return plug 20 has a leading end 20a that is closer to the electrosurgical generator 110 when the return plug 20 is connected to the return terminal 116 and a trailing end 20b opposite the leading end 20a that is further away from the electrosurgical generator 110 when the return plug 20 is connected to the return terminal 116. The return plug 20 has a housing formed of a first or lower housing 22 and a second or upper housing 23. The upper and lower housings 22, 23 have a connection system 25 for aligning and securing the upper and lower housings 22, 23 together. As shown, the lower housing 22 includes one or more openings that receive posts of the upper housing 23 such that when the posts are received within the openings, the upper and lower housings 22, 23 are aligned with and secured to one another. Other connection mechanisms are also contemplated.

The upper and lower housings 22, 23 together define two return channels 24 and a plunger channel 28 positioned between the return channels 24. Each channel 24, 28 is open at the leading end 20a of the upper and lower housings 22, 23. Each return channel 24 is configured to receive a portion of the return cable 70 therein. Each return channel 24 may be configured to have an interference fit with the portion of the return cable 70 to prevent the return cable 70 from withdrawing from the return plug 20. Additionally or alternatively, each return channel 24 may include a suitable shape or other feature(s) to prevent the portion of the return cable 70 from withdrawing from the return plug 20.

Each return channel 24 includes a leading portion 24a, a transverse portion 24b, and a trailing portion 24c. Each leading portion 24a extends from the leading end 20a in a direction parallel to the other leading portion 24a. Each transverse portion 24b extends from one of the leading portions 24a and away from the other transverse portion 24b such that trailing ends of the transverse portions 24b are spaced apart from one another a greater distance than leading ends of the transverse portions 24b. Each trailing portion 24c extends from one of the transverse portions 24b through the trailing end 20b of the return plug 70 in a direction parallel to the other.

The plunger channel 28 is positioned between the return channels 24 and extends from the leading end 20a of the return plug 70 towards the trailing end 20b of the return plug 70 in a direction parallel to the leading portions 24a and the trailing portions 24b of the return channels 24. The plunger channel 28 includes a leading portion 28a, a central portion 28b, and a trailing portion 28c. The leading portion 28a extends from the leading end 20a of the return plug 70 and is limited in the transverse directions by lateral walls. The trailing portion 28c is positioned between the central portion 28b and the trailing end 20c of the housing. The trailing portion 28c is defined in the transverse directions by lateral walls and in a longitudinal direction by a trailing wall that defines a distal end of the trailing portion 28c. The central portion 28b is positioned between the leading portion 28a and the trailing portion 28c and has a post 29 extending from the lower housing 22 towards the upper housing 23 at a leading end thereof and a bar conductor 37 extending between the lateral walls defining the trailing portion 28c at a trailing end thereof. The central portion 28b may extend laterally to walls defining the return channels 24.

Figure 3:
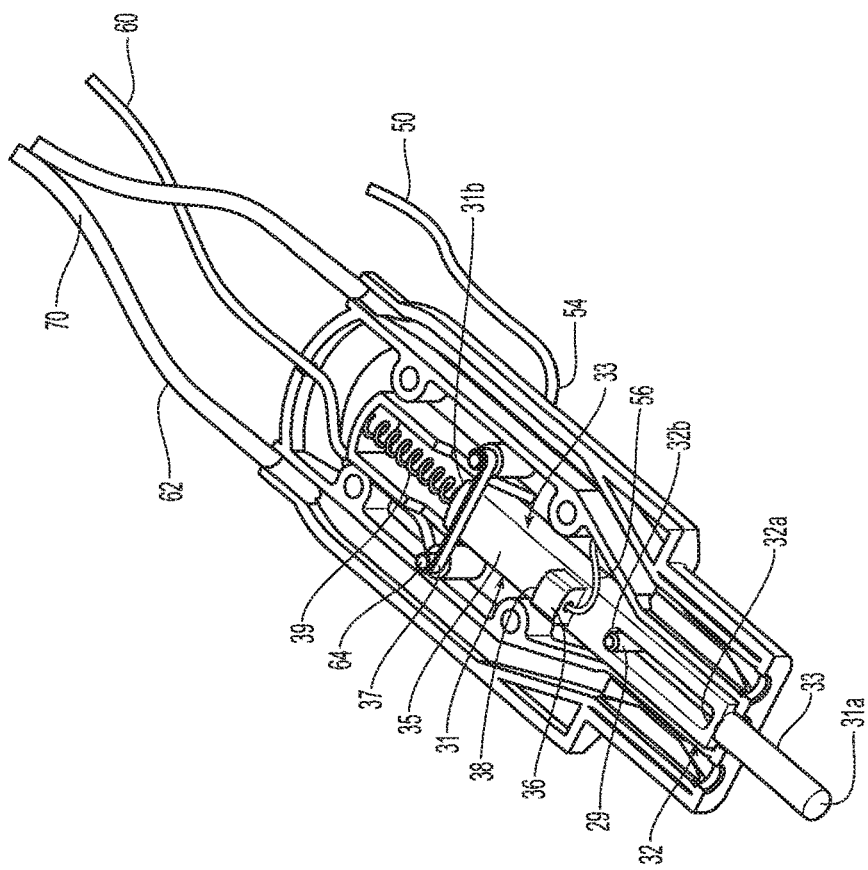
FIG. 3 is a perspective view with a top cover removed showing the internals of the plug of FIG. 2 in a disengaged configuration.

With additional reference to FIG. 3, the plunger channel 28 receives the mechanical switch mechanism 30 therein. The switch mechanism 30 includes a plunger 31, the bar conductor 37, and a biasing member 39. The plunger 31 is disposed within the plunger channel 28 and is translatable in a direction extending between the leading and trailing ends 20a, 20b of the housing. The biasing member 39 is disposed within the trailing portion 28c of the plunger channel 28 and is configured to urge the plunger 31 towards the leading end 20a of the return plug 70.

Figure 4:
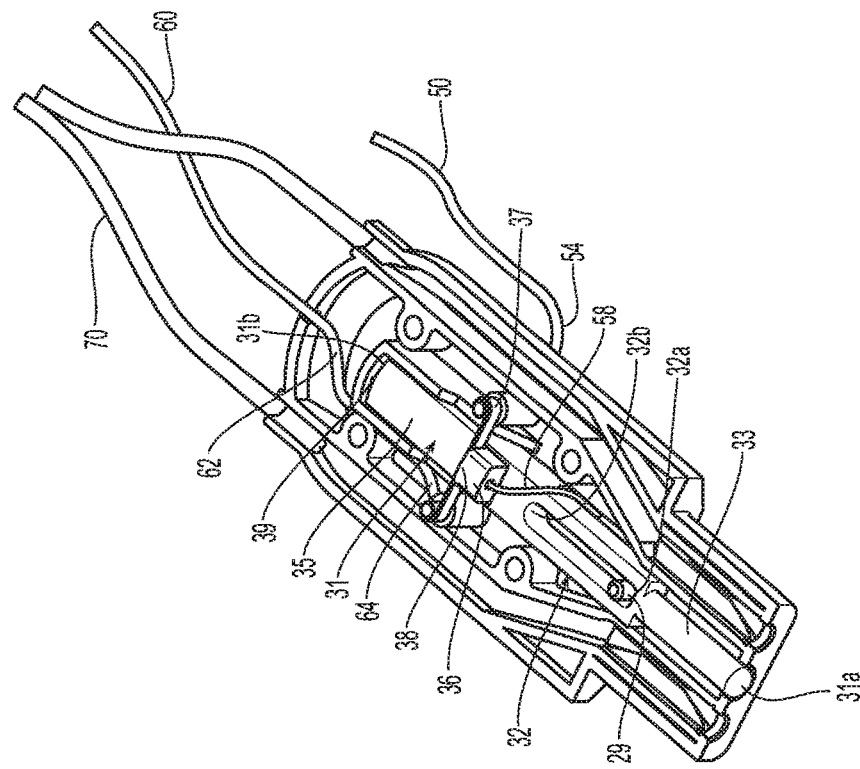
FIG. 4 is a perspective view with a top cover removed showing the internals of the plug of FIG. 2 in an engaged configuration.

With particular reference to FIG. 2, the plunger 31 includes a body having, from a leading tip 31a to a trailing end 31b, a tip portion 33, a trailing portion 35, and a slot 32 defined therebetween. The slot 32 is configured to slidably receive the post 29 therein and includes a leading stop 32a and a trailing stop 32b. The post 29 limits translation of the plunger 31 between a disengaged position in which the tip portion 33 extends or further extends from the leading end 20a of the return plug 70 as shown in FIG. 3 and an engaged position in which the tip portion 33 is disposed substantially within or more-retracted within the leading portion 28a of the plunger channel 38 as shown in FIG. 4. In the disengaged position the post 29 may contact the trailing stop 32b of the slot 32 and in the engaged position the post 29 may contact the leading stop 32b of the slot 32.

The trailing portion 35 of the plunger 31 includes a protrusion 36 extending from an upper surface of the trailing portion 35 facing the upper housing 23, an active connector 34 adjacent the trailing stop 32b of the slot 32, and a contact 38 on a surface of the protrusion 36 facing the trailing end 20b of the return plug 70. The active connector 34 may be positioned within the slot 32, may be on or in a lower surface of the plunger 31 facing the lower housing 22, or may be on or in a side surface of the plunger 31 facing one of the return channels 24. The active connector 34 extends through the body of the plunger 31 and is electrically coupled to the contact 38. The active connector 34 may pass through a portion of the protrusion 36.

With continued reference to FIGS. 2 and 3, the active wire 54 of the active plug 50 includes a link 56 that extends into the interior of the return plug 70. The link 56 may pass through the lower housing 22, the upper housing 23, or therebetween, to enter the interior of the return plug 70. The link 56 is coupled to the active connector 34 of the plunger 31 such that the prongs 52 (FIG. 1) of the active plug 50 are in electrical communication with the contact 38 of the plunger 31.

The lead 62 of the active cable 60 includes a link 64 that extends into the interior of the return plug 70. The link 64 may pass through the trailing end 20b of the upper or lower housing 22, 23 to enter the interior of the return plug 70. In some embodiments, the link 64 passes through the upper or lower surface of the upper or lower housing 22, 23 respectively. The link 64 is coupled to the bar conductor 37 such that the active electrode 122 (FIG. 1) of the electrosurgical instrument 120 is in electrical communication with the bar conductor 37. As shown, the link 64 may pass between one of the return channels 24 and the plunger channel 28 to couple to the bar conductor 37. In some embodiments, the link 64 may pass through the wall defining the trailing end of the plunger channel 28 to couple to the bar conductor 37. The bar conductor 37 is secured between the upper and lower housings 22, 23 with each end portion of the bar conductor 37 longitudinally and laterally fixed within the return plug 70. The bar conductor 37 has a conductive outer surface and may be formed of an entirely conductive material. The bar conductor 37 may be flexible and/or may be elastic. In some embodiments, the bar conductor 37 is a leaf spring such that the bar conductor 37 cooperates with the biasing member 39 to urge the plunger 31 towards the leading end 20a of the return plug 70 when contacted by the contact 38 as detailed below.

Referring to FIG. 3, in the disengaged position, the biasing member 39 urges the plunger 31 towards the leading end 20a of the return plug 20 such that the tip portion 33 extends from the leading end 20a. When the plunger 31 is in the disengaged position, the contact 38 is spaced apart from the bar conductor 37 such that there is no electrical communication between the prongs 52 (FIG. 1) of the active plug 50 and the active electrode 122 (FIG. 1) of the electrosurgical instrument 120. The slot 32 of the plunger 31 is sized such that in the disengaged position, the distance between the contact 38 and the bar conductor 37 is large enough to prevent any electrical communication or coupling therebetween.

With reference to FIG. 4, in the engaged position, the plunger 31 is translated towards the trailing end 20b of the return plug 70 against the biasing member 39 such that the contact 38 contacts the bar conductor 37 to electrically couple the prongs 52 (FIG. 1) of the active plug 50 with the active electrode 122 (FIG. 1) of the electrosurgical instrument 120. The plunger 31 may be translated towards the trailing end 20b such that the contact 38 bends or flexes a portion of the bar conductor 37 towards the trailing end 20b of the return plug 70. The flexing of the bar conductor 37 may increase a contact area between the contact 38 and the bar conductor 37 as the bar conductor 37 bends around the protrusion 36.

Referring to FIGS. 1-4, the use of the electrosurgical system 1 is detailed. Initially, the active plug 50 is connected to the electrosurgical generator 110 such that the prongs 52 are received within the receptacles 114 of the active terminal 112. As detailed above, when the prongs 52 are received within the receptacles 114, the active plug 50 is in electrical communication with the active terminal 112 of the electrosurgical generator 110. With the active plug 50 connected to the electrosurgical generator 110 and the return plug 20 disconnected, the active electrode 122 is out of electrical communication with the active terminal 112 of the electrosurgical generator 110 as a result of the switch mechanism 30 being in the disengaged position when the return plug 20 is disconnected from the return terminal 116.

With the active plug 50 connected to the electrosurgical generator 110, the return plug 20 is connected to the return terminal 116 of the electrosurgical generator 110. To connect the return plug 20, the return prongs 118 of the return terminal 116 are received within the return channels 24 of the return plug 20. As the return prongs 118 are received within the return channels 24, the tip portion 33 of the plunger 31 engages return terminal 116 to translate the plunger 31 of the switch mechanism 30 from the disengaged position towards the trailing end 20b of the return plug 20 as the return prongs 118 are received within the return channels 24 to translate the plunger 31 of the switch mechanism 30 to the engaged position such that the contact 38 is in electrical communication with the bar conductor 37.

As detailed above, when the switch mechanism 30 is in the engaged position and the active plug 50 is connected to the active terminal 112 of the electrosurgical generator 110, the active electrode 122 is in electrical communication with the active terminal 112. With the active electrode 122 in electrical communication with the active terminal 112, the electrosurgical instrument 120 can be used to deliver electrosurgical energy to tissue using the active electrode 122 which is returned to the electrosurgical generator 110 via the return device 130. The return device 130 may be positioned within a surgical site adjacent the active electrode 120 or may be a return pad in contact with the skin of the patient. In addition, if the return plug 20 comes loose or is disconnected form the return terminal 116, the biasing member 139 translates the plunger 31 towards the leading end 20a of the return plug 20 such that the contact 38 breaks the connection with the bar conductor 37 such that the electrical communication between the active electrode 122 and the active terminal 112 is broken. As a result, delivery of electrosurgical energy from the electrosurgical generator 110 is prevented if the return plug 20 is not re-connected to the return terminal 116.

Figure 5:
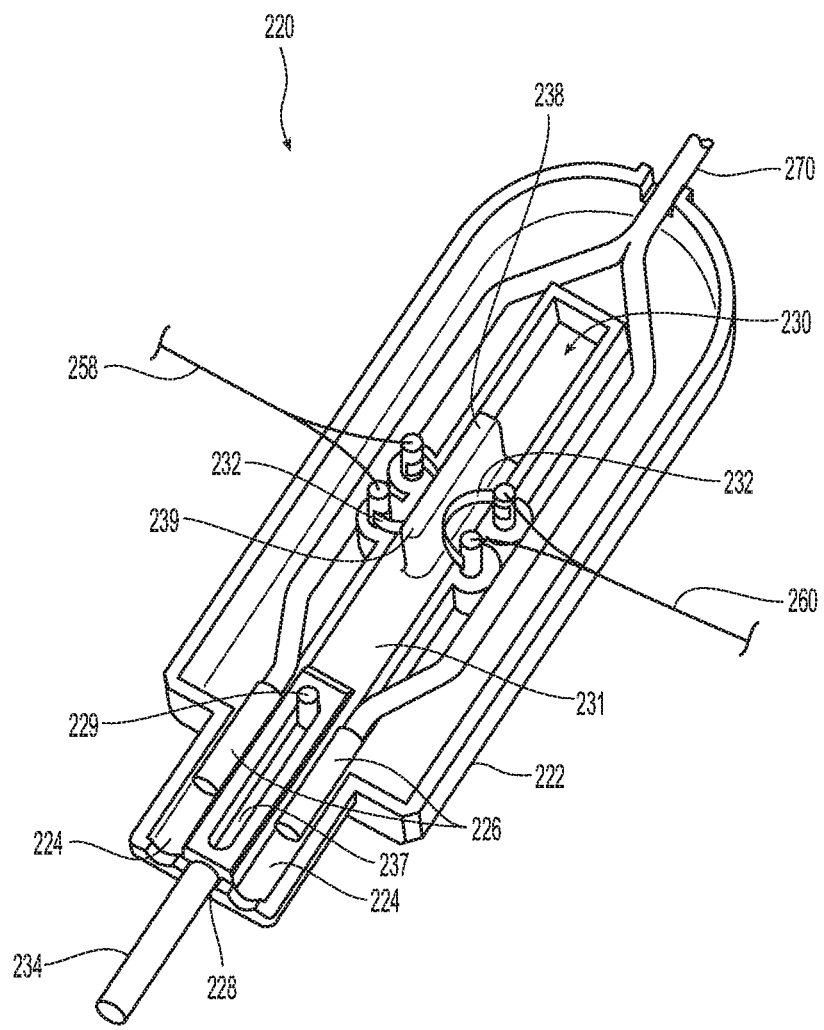
FIG. 5 is a perspective view with a top cover removed showing the internals of another plug in accordance with the present disclosure configured for use with the electrosurgical system of FIG. 1, wherein the plug is disposed in a disengaged configuration.
Figure 6:
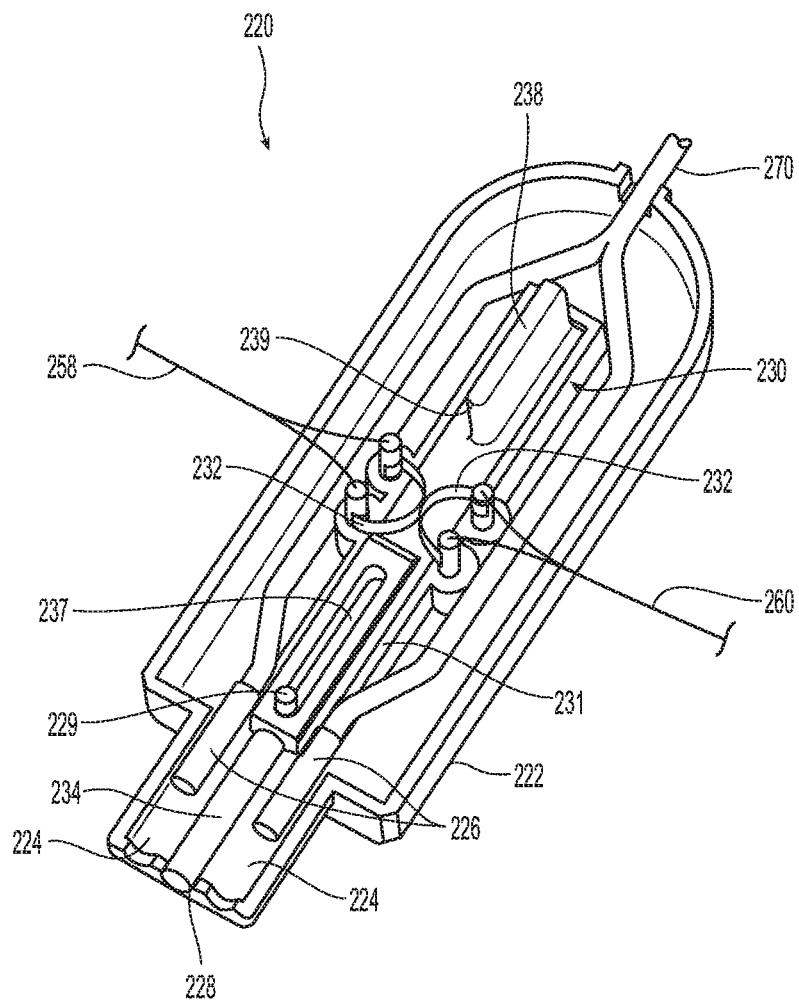
FIG. 6 is a perspective view with a top cover removed showing the internals of the plug of FIG. 5, wherein the plug is disposed in a disengaged configuration.

Referring to FIGS. 5 and 6, another embodiment of a return plug 220 configured for use with electrosurgical system 1 (FIG. 1) or any other suitable electrosurgical system is shown. With additional reference to FIG. 1, the return plug 220 includes a mechanical switch mechanism 230 to electrically couple the active plug 50 with the active cable 60 when the return plug 220 is connected to the return terminal 116 of the electro surgical generator 110 such that electrosurgical energy can be delivered to tissue by the active electrode 122, similarly as detailed above with respect to return plug 20. The mechanical switch mechanism 230 prevents delivery of electrosurgical energy to the active electrode 122 when the return plug 220 is not connected to the return terminal 116, also similarly as detailed above with respect to return plug 20. As the function of return plug 220 as part of electrosurgical system 1 is similar to that of return plug 20, only the differences between return plug 220 and return plug 20 are described in detailed hereinbelow, while similarities are summarily described or omitted entirely.

Continuing with reference to FIGS. 5 and 6, return plug 220 has a housing 222 formed of a lower housing and an upper housing (the upper housing is removed in FIGS. 5 and 6 to illustrate the internal features of return plug 220). Housing 222 defines two return channels 224 and a plunger channel 228 positioned between the return channels 224. A portion of the return cable 270 is received within each of the return channels 224, terminating at respective contacts 226 disposed within the return channels 224. Return channels 224 are configured to receive return prongs 118 of return terminal 116 of electrosurgical generator 110 (see FIG. 1) to thereby electrically connect return terminal 116 (FIG. 1) with contacts 226 and, thus, return cable 270, thereby ultimately connecting return terminal 116 and return device 130 with one another (see FIG. 1). Plunger channel 228, as noted above, is positioned between the return channels 224 and slidably receives a plunger 231 of the mechanical switch mechanism 230.

The mechanical switch mechanism 230 includes plunger 231 and a pair of spring contacts 232 mounted within housing 222 and disposed on either side of the plunger 231. One of the spring contacts 232 is electrically coupled to the electrosurgical device 120 (FIG. 1) via an active cable 260 while the other spring contact 232 is electrically coupled to the active plug 50 (FIG. 1) via a connector cable 258. In this manner, when spring contacts 232 are disconnected from one another, energy is inhibited from being supplied to the electrosurgical device 120 (FIG. 1) even when the active plug 50 (FIG. 1) is connected to the electrosurgical generator 110 (FIG. 1). Once spring contacts 232 are connected with one another, thereby connecting connector cable 258 and active cable 260, energy may be supplied from the electro surgical generator 110 (FIG. 1) to the electrosurgical device 120 (FIG. 1) provided the active plug 50 (FIG. 1) is coupled to the electrosurgical generator 110 (FIG. 1). Spring contacts 232 are biased towards one another to a contacting, connected configuration such that, in the absence of an interrupting structure disposed between spring contacts 232, spring contacts 232 are electrically coupled with one another (and, thus, connector cable 258 and active cable 260 are electrically coupled with one another). In the biased position of spring contacts 232, each spring contact 232 may define a semi-circular configuration wherein the convex outer surfaces thereof abut one another to establish the electrical communication therebetween. Spring contacts 232 may be configured as flat springs formed from sheets of strips of electrically-conductive material, as shown, or may define any other suitable configuration.

Plunger 231 includes a proximal head portion 234, a body portion 236 defining a slot 237, and a distal fin portion 238 that is at least partially formed from and/or coated with an electrically insulative material. A peg 229 of housing 222 extends into plunger channel 228 and is received within slot 237 of body 236 of plunger 231 to limit plunger 231 to a range of longitudinal motion through plunger channel 238 between an extended position (FIG. 5) and a retracted position (FIG. 6).

In the extended position of plunger 231 (FIG. 5), proximal head portion 234 of plunger 231 extends proximally from plunger channel 228 to protrude proximally from housing 222, and distal fin portion 238 is interdisposed between spring contacts 232, thereby acting as an interrupting structure maintaining spring contacts 232 in a disconnected configuration. As noted above, distal fin portion 238 is at least partially formed from and/or coated with an electrically insulative material to inhibit indirect electrical communication between spring contacts 232 via distal fin portion 238.

In the retracted position of plunger 231 (FIG. 6), on the other hand, proximal head portion 234 of plunger 231 is retracted at least partially (in some embodiments, fully) into plunger channel 228 and distal fin portion 238 is distally-spaced from spring contacts 232, thereby allowing spring contacts 232 to return under their bias into contact and, thus, electrical communication, with one another. Plunger 231 may be biased towards the extended position (FIG. 5) such that, in the absence of sufficient urging of proximal head portion 234 of plunger 231 towards the retracted position, spring contacts 232 are disconnected from each other.

Referring to FIGS. 1, 5, and 6, in use, the active plug 50 is connected to the electrosurgical generator 110. With the active plug 50 connected to the electrosurgical generator 110 and the return plug 220 still disconnected, the active electrode 122 is out of electrical communication with the active terminal 112 of the electrosurgical generator 110 as a result of the switch mechanism 230 being in the disengaged position (and, thus, the spring contacts 232 disconnected; see FIG. 5).

The return plug 220 is connected to the return terminal 116 of the electrosurgical generator 110 by inserting the return plug 220 into the return terminal 116 such that the return prongs 118 of the return terminal 116 are received within the return channels 224 of the return plug 220 and contact the respective contacts 226 disposed therein, thereby electrically coupling the return terminal 116 with the return cable 270. As the return prongs 118 are received within the return channels 224, proximal head portion 234 of plunger 231 engages return terminal 116 (or other structure associated with the electrosurgical generator 110) to urge the plunger 231 from the extended position to the retracted position. Thus, plunger 231 is retracted at least partially (in some embodiments, fully) into plunger channel 228 whereby distal fin portion 238 is distally-spaced from spring contacts 232. As distal fin portion 238 is displaced from between spring contacts 232, spring contacts 232 return under their bias into contact and, thus, electrical communication, with one another (see FIG. 6) to electrically couple the active electrode 122 with the active terminal 112 of the electrosurgical generator 110.

When the return plug 220 is removed from the return terminal 116, the plunger 231 is returned to the extended position (FIG. 5), whereby distal fin portion 238 separates and extends between spring contacts 232, disconnecting spring contacts 232 from one another, thereby disconnecting the active electrode 122 from the active terminal 112. To this end, distal fin portion 238 may include a tapered proximal end 239 to facilitate urging spring contacts 232 apart from one another and positioning of distal fin portion 238 therebetween as plunger 231 moves from the retracted position (FIG. 6) to the extended position (FIG. 5).

Figure 7:
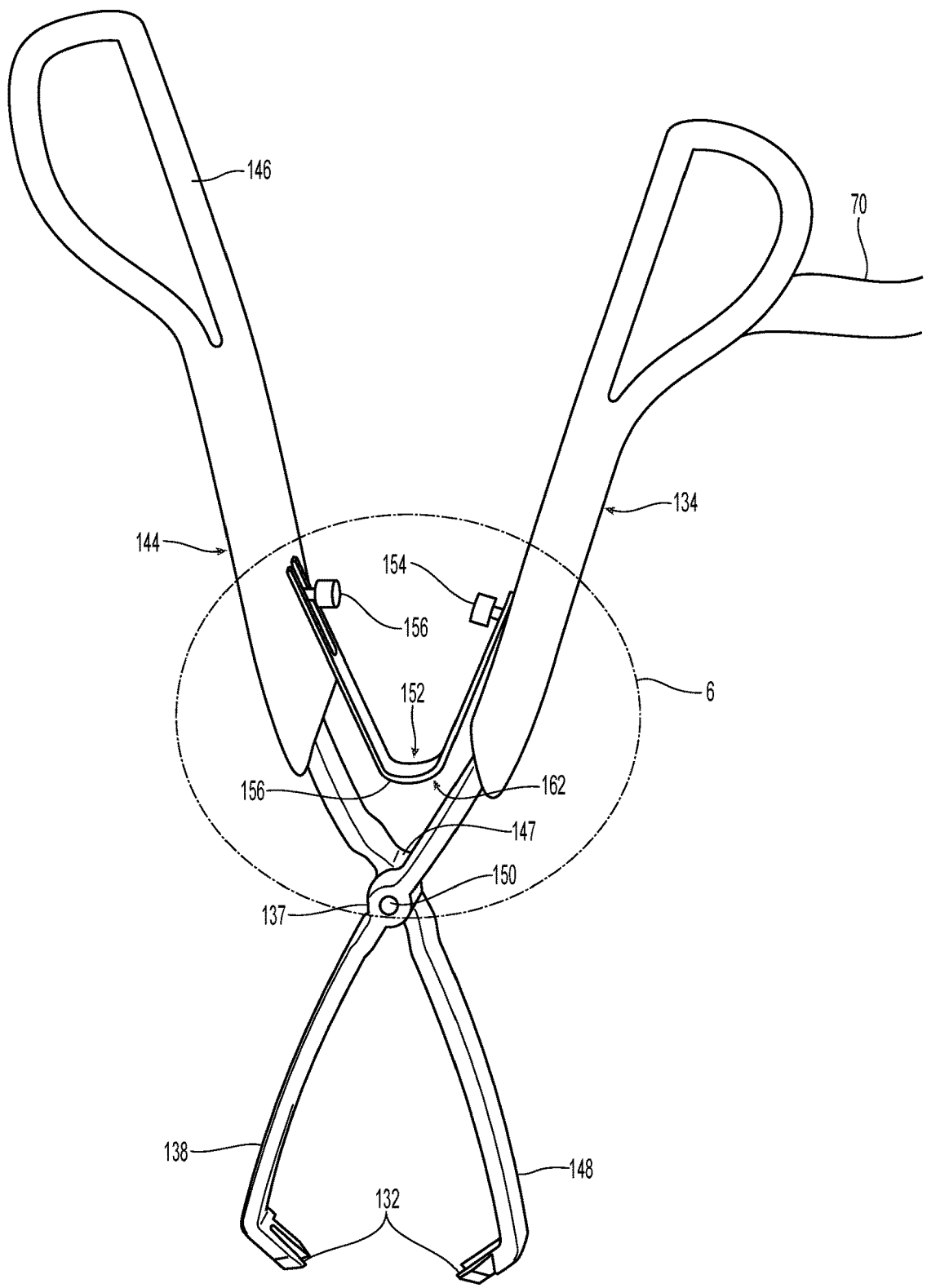
FIG. 7 is a perspective view of a return device of the electrosurgical system of FIG. 1.

With reference to FIG. 7, an embodiment of the return device 130 is described in accordance with the present disclosure. The return device 130 includes a first arm 134 and a second arm 144 that are pivotally coupled to one another by a pivot pin 150. Specifically, the first arm 134 includes a proximal handle portion 136 and a distal grasper portion 138 with a pivot portion 137 positioned between the proximal handle portion 136 and the distal grasper portion 138. Similarly, the second arm 144 includes a proximal handle portion 146 and a distal grasper portion 148 with a pivot portion 147 positioned between the proximal handle portion 146 and the distal grasper portion 138. The proximal handle portions 136, 146 are coated with or formed of an insulative material to isolate a clinician using the return device 130 from an electrical energy of the grasper portions 138, 148. A portion of each grasper portion 138, 148 and/or the pivot portions 137,147 may be formed of or coated with a conductive material to act as a return electrode 132 as detailed above. One or both of the grasper portions 138, 148 may be in electrical communication with the return cable 70 that is connected to one of the arms, e.g., the first arm 134 as shown. The return cable 70 may be connected to the first arm 134 in or adjacent the handle portion 136 and be coated with an insulative material to isolate electrical energy from a clinician. In embodiments, the return cable 70 is connected to the first arm 134 within the handle portion 136 such that the entire grasper portion 138 and the pivot 137 of the first arm 134 is in electrical communication with the return cable 70. In embodiments where the pivot portions 137, 147 are constructed of or coated with a conductive material, contact between the pivot portions 137, 147 places the pivot portion 147 and the grasper portion 148 of the second arm 144 in electrical communication with the return cable 70. The pivot pin 150 extends through and pivotably couples pivot portions 137, 147 and may be formed of or coated with a conductive material to place the pivot portions 137, 147 in electrical communication with one another. In particular embodiments, the return cable 70 is connected directly to each of the first and second arms 134, 144.

Figure 8:
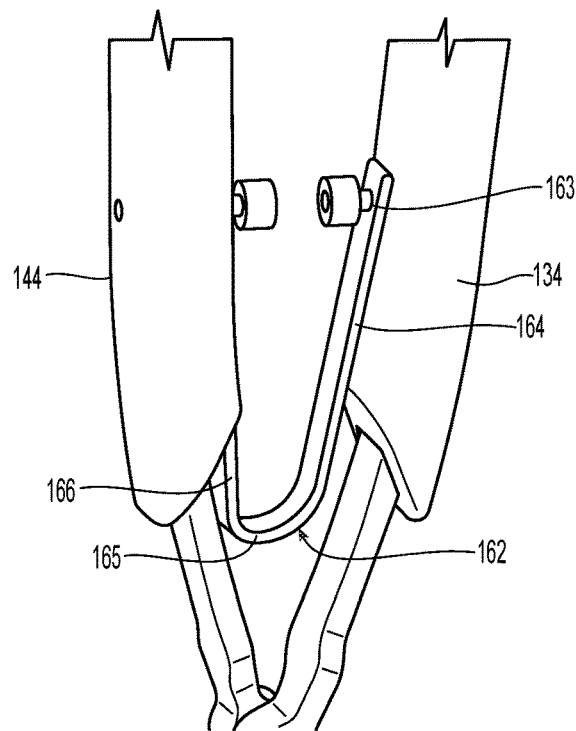
FIG. 8 is an enlarged perspective view of a portion of the return device as indicated in FIG. 7.
Figure 9:
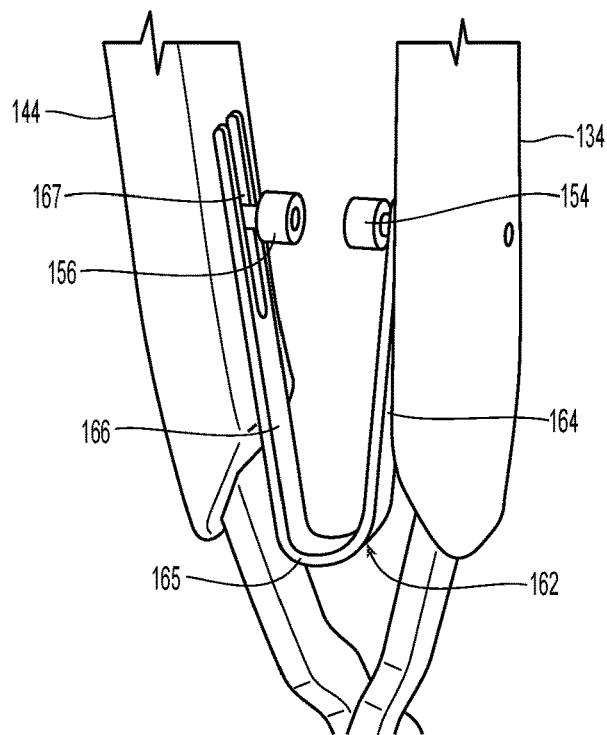
FIG. 9 is another enlarged perspective view of a portion of the return device as indicated in FIG. 7.

With additional reference to FIGS. 8 and 9, the return device 130 includes an opening/locking device 162 positioned between the first and second arms 134, 144. The opening/locking device 162 is in the form of a leaf spring having a first portion 164 adjacent the first arm 134, a second portion 166 adjacent the second arm 144, and a central portion 165 interconnecting the first and second portions 164, 166. The opening/locking device 162 has an operating configuration in which the opening/locking device 162 is configured to urge the first and second handle portions 136, 146 away from one another such that the grasping portions 138, 148 are also urged apart from one another. The opening/locking device 162 may also have a locked configuration in which the opening/locking device 162 is configured to fix the first and second handle portions 136, 146 and thus, the grasping portions 138, 148 in a fixed position relative to one another. The opening/locking device 162 may be electrically isolated from the grasping portions 138, 148 of the first and second arms 134, 144 by the first and second handle portions 136, 146. The first and second portions 164, 166 extend towards the pivot pin 150 and are connected to one another by the central portion 165.

The first portion 164 defines a hole 163 that receives a first fastener 154. The first fastener 154 passes through the hole 163 to secure the first portion 164 to the first arm 134. The hole 163 is configured to complement the first fastener 154 such that first portion 164 is substantially fixed to the first arm 134 by the first fastener 154. The first fastener 154 may be threaded into the first arm 134 to secure the first portion 164 to the first arm 134. The first fastener 154 secures the first portion 164 to the first arm 134 and prevents the first portion 164 from translating longitudinally, transversely, or away from the first arm 134.

The second portion 166 defines a longitudinal slot 167 that receives the second fastener 156. The second fastener 156 passes through the slot 167 to secure the second portion 166 to the second arm 144. The longitudinal slot 167 is configured to receive the second fastener 156 such that the second portion 166 is configured to translate in a longitudinal direction along the second arm 144 as the first and second arms 134, 144 are moved towards and away from one another about the pivot 150. The second fastener 156 may be threaded into the second arm to secure the second portion 166 to the second arm 134. In the operating configuration, the second fastener 156 secures the second portion 166 to the second arm 144 such that the second portion 166 translates in a longitudinal direction along the second arm 144, e.g., towards and away from the pivot pin 150, as the first and second arms 134, 144 are pivoted relative to one another while preventing the second portion 166 from translating transversely or away from the second arm 144. In the locked configuration, the second fastener 156 is tightened such that the second portion 166 secures the second portion to the second arm 144 and prevents the second portion 166 from translating longitudinally, transversely, or away from the second arm 144.

As detailed above, the opening/locking device 162 may be used with the return device 130; however, the opening/locking device 162 may also be used with a plurality of other graspers or scissor type devices to selectively lock pivoting arms relative to one another and to bias the pivoting arms apart from one another.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. An electrosurgical system comprising:
   an electrosurgical generator including an active terminal and a return terminal;
   an electrosurgical instrument including an active electrode;
   a return instrument including a return electrode;
   an active plug configured to connect to the active terminal of the electrosurgical generator;

a return plug configured to connect to the return terminal of the electrosurgical generator to electrically couple the return electrode to the return terminal;

an active cable extending from the return plug to the electrosurgical instrument, the active cable in electrical communication with the active electrode;

a return cable extending from the return plug to the return instrument;

a connector cable extending from the active plug to the return plug; and a mechanical switch mechanism disposed within the return plug, the mechanical switch mechanism having a disengaged position in which the active plug is electrically disconnected from the active cable and an engaged position in which the active plug is in electrical communication with the active cable.

2. The electrosurgical system according to claim 1, wherein the mechanical switch mechanism is in the disengaged position when the return plug is disconnected from the return terminal and is in the engaged position when the return plug is connected to the return terminal.

3. The electrosurgical system according to claim 1, wherein the mechanical switch mechanism includes a plunger translatable within the return plug, the plunger including a tip portion extending from a leading end of the return plug in the disengaged position and disposed within the return plug in the engaged position.

4. The electrosurgical system according to claim 3, wherein the tip portion is configured to engage the return terminal as the return plug is connected to the return terminal such that engagement between the tip portion and the return terminal transitions the mechanical switch mechanism from the disengaged position to the engaged position.

5. The electrosurgical system according to claim 3, wherein the return plug includes a post and the plunger includes a slot defined therethrough, the post received within the slot to limit translation of the plunger towards and away from the leading end of the return plug.

6. The electrosurgical system according to claim 3, wherein the return plug defines a plunger channel, the plunger slidably received within the plunger channel.

7. The electrosurgical system according to claim 6, wherein the mechanical switch mechanism includes a biasing member disposed within the plunger channel and engaged with the plunger to urge the plunger towards the leading end of the return plug.

8. The electrosurgical system according to claim 6, wherein the mechanical switch mechanism includes a bar conductor extending across the plunger channel, the bar conductor electrically coupled to the active cable.

9. The electrosurgical system according to claim 8, wherein the bar conductor is a leaf spring.

10. The electrosurgical system according to claim 8, wherein the plunger includes a protrusion having a contact on a surface facing a trailing end of the return plug, the contact spaced apart from the bar conductor in the disengaged position and in contact with the bar conductor in the engaged position.

11. The electrosurgical system according to claim 10, wherein in the engaged position, engagement between the contact and the bar conductor bends the bar conductor towards the trailing end of the return plug.

12. The electrosurgical system according to claim 10, wherein the active plug includes an active lead that extends into the return plug and is coupled to the plunger such that the active lead is in electrical communication with the contact.

13. The electrosurgical system according to claim 12, wherein the active lead is connected to a leading surface of the protrusion opposite the contact.

14. A return plug for an electrosurgical system, the return plug comprising:

a mechanical switch mechanism for mechanically connecting an active lead configured to electrically connect to an active terminal of an electrosurgical generator to an active cable configured to electrically connect to an active electrode of an electrosurgical instrument when the return plug is connected to a return terminal of the electrosurgical generator and to electrically disconnect the active lead from the active cable when the return plug is not connected to the return terminal; and an upper housing and a lower housing defining a pair of return channels and a plunger channel defined between the pair of return channels, each of the return channels extending through a leading end and a trailing end of the upper and lower housings.

15. The return plug according to claim 14, wherein the mechanical switch mechanism includes a plunger slidably disposed within the plunger channel, the plunger including a slot defined therethrough configured to allow translation of the plunger between a first position in which the active lead is electrically disconnected from the active cable and a second position in which the active lead is electrically connected to the active cable.

16. The return plug according to claim 15, wherein the plunger is biased towards the first position.

17. An electrosurgical system comprising:
a first electrosurgical device;
a second electrosurgical device;
a first plug;
a second plug;
a first cable extending from the second plug to the first electrosurgical device;
a second cable extending from the second plug to the second electrosurgical device;
a connector cable extending from the first plug to the second plug; and
a switch mechanism disposed within the second plug, the switch mechanism having a first condition in which the first plug is electrically disconnected from the first cable and a second condition in which the first plug is in electrical communication with the first cable.

18. The electrosurgical system according to claim 17, wherein one of the first electrosurgical device or the second electrosurgical device is configured to conduct electrosurgical energy having a first electrical potential to tissue and wherein the other of the first electrosurgical device or the second electrosurgical device is configured to collect electrosurgical energy having a different electrical potential conducted through tissue.

19. The electrosurgical system according to claim 17, wherein the switch mechanism includes a mechanical switch component movable between a first position, corresponding to the first condition, and a second position, corresponding to the second condition.

* * * * *